United States Patent
Fujii et al.

(10) Patent No.: US 6,277,971 B1
(45) Date of Patent: Aug. 21, 2001

(54) NEF-ATTACHABLE PROTEIN, DNA ENCODING THE PROTEIN AND A MONOCLONAL ANTIBODY AGAINST SAID PROTEIN

(75) Inventors: Yoichi Fujii, Nagoya; Kaori Otake, Kani, both of (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/333,521

(22) Filed: Jun. 15, 1999

(30) Foreign Application Priority Data

Jun. 15, 1998 (JP) .................................................. 10-185708

(51) Int. Cl.$^7$ .................................................. C07H 21/02
(52) U.S. Cl. .............................. 536/23.1; 435/5; 435/7.1; 435/974; 514/44; 530/350; 935/19
(58) Field of Search .................................. 424/148.1, 160; 435/5, 7.1, 974; 530/324, 350; 536/23.5, 23.1; 514/44; 935/19

(56) References Cited

U.S. PATENT DOCUMENTS

| | | | |
|---|---|---|---|
| 4,816,397 | 3/1989 | Boss et al. | 435/68 |
| 4,816,567 | 3/1989 | Cabilly et al. | 530/387 |
| 5,225,539 | 7/1993 | Winter | 530/387.3 |

FOREIGN PATENT DOCUMENTS

| | | |
|---|---|---|
| 0 120 694 B1 | 10/1984 | (EP) . |
| 0 125 023 B1 | 11/1984 | (EP) . |
| 0 239 400 A2 | 9/1987 | (EP) . |
| 2 720 068 | 11/1995 | (FR) . |
| WO 86/01533 | 3/1986 | (WO) . |
| WO 98 13377 | 4/1998 | (WO) . |

OTHER PUBLICATIONS

Lui et al.; Binding of HIV–1 Nef to a novel thioesterase enzyme correlates with Nef–mediated CD4 down–regulation. The Journal of Biological Chemistry vol. 272, (1997) p. 13779–13785.*

Cawthon et al.; cDNA sequence and genomic structure of EV12B, a gene lying within an intron of the neurofibromtosis type 1 gene. Genomics vol. 9. (1991) p. 446–460.*

Ahn et al.; The structural and functional diversity of dystophin. Nature Genetics vol. 3, (1993) p. 283–291.*

Okada H., et al., "Inhibition of HIV–1 Nef induced apoptosis of uninfected human blood cells by serine/threonine protein kinase inhibitors, fasudil hydrochloide and M3" *FEBS LETTERS*, vol. 422, No. 3, Feb.6, 1998, pp.363–367, XP002115665, Amsterdam, NL.

Luo T., et al., "Infectivity enhancement by immunodeficiency virus type 1 Nef is independent of its association with a cellular serine/threonine kinase" *Journal of Virology*, vol. 71, No. 12, 1997, pp. 9524–9530, XP002115666 US.

Rossi F., et al., "H$_5$N3 proteasomal subunit as a target for human immunodeficiency virus type 1 Nef protein" *Virology*, vol. 237, No. 1, 1997, pp. 33–45, XP002115667, Orlando, US.

Smith B.L., et al., "The HIV Nef protein associates with protein kinase C theta" *Journal of Biological Chemistry*, vol. 271, No. 28, 1996, pp. 16753–16757, XP002115668, MD US.

Fujii, Y. et al., "Biological Overview of HIV Accessory Protein Nef," *Saibo Kogaku*, vol. 16, No. 1, pp. 94–99 (1997).

Patent Abstracts of Japan, vol. 017, No. 225 (C–1055), May 10, 1993 & JP 04360838.

De Reuck et al., "A double–blind study of neurotropin in patients with acute ischemic stroke," in *Acta Neurol Scand*, 89, pp. 329–335 (1994).

* cited by examiner

Primary Examiner—Jeffrey Stucker
Assistant Examiner—Ulrike Winkler
(74) Attorney, Agent, or Firm—Hollander Law Firm, P.L.C.

(57) ABSTRACT

A monoclonal antibody specific to Nap was prepared by using a crude membrane fraction from a cell line which has a high affinity to Nef as an antigen. A cDNA clone which encodes Nap was obtained by screening a cDNA library of said cell line utilizing the specific antibody. The nucleotide sequence of this cDNA was elucidated whereupon the full amino acid sequences of human Nap was identified. Since the anti-Nap monoclonal antibody inhibits the binding of Nef to Nap, it can be used as a new therapeutic agent for AIDS. In addition, it can be applied for the diagnosis of AIDS by clarifying the relation between the expression of Nap and the development of AIDS. Nap can be utilized for binding experiments to Nef. It is useful for the development of novel therapeutic agents for AIDS based upon a mechanism of action which inhibits the attachment of both factors and development of new inhibitors against the onset of AIDS by a mechanism of action different from that of reverse transcriptase inhibitors or protease inhibitors.

6 Claims, 1 Drawing Sheet

NEF-ATTACHABLE PROTEIN, DNA ENCODING THE PROTEIN AND A MONOCLONAL ANTIBODY AGAINST SAID PROTEIN

FIELD OF THE INVENTION

The present invention relates to a Nef-attachable protein which is useful for diagnosis, therapy and development of a therapeutic agent for AIDS, to a gene encoding the protein and to a monoclonal antibody against said protein.

BACKGROUND OF THE INVENTION

In general, retroviruses have the proteins Gag, Pol, and Env in common. In addition to these proteins, human immunodeficiency virus (HIV) has viral-specific regulatory proteins and accessory proteins. Nef is one of the accessory proteins which is specific to HIV-1, HIV-2 and SIV (simian immunodeficiency virus) and is synthesized in the early stage of the virus replication. The protein was designated Nef at the beginning since it is deemed that Nef is a negative factor which decreases the replication of the virus. However, afterward, it has been suggested that Nef works as a positive regulator for HIV replication by experiments testing the pathogenesis of Nef-deleted SIV mutant in the rhesus monkey. Nef is recognized anew as an important factor for holding a key to developing the pathogenesis of AIDS. See, Fujii et al, *Saibo Kogaku*, vol. 16, No. 1, 94–99 (1997)].

As mentioned in detail in the above article by Fujii, et al., the important functions of Nef in vivo are thought to be: (1) promotion of virus replication, (2) down regulation of CD4 molecularly, and (3) cytotoxicity to T cells. With regard to the virus infection, it has been known that Nef has an affinity to cell membranes, is necessary for virus adsorption and the invasion of the virus into cells, and participates in viral DNA synthesis. Concerning the cytotoxicity to T cells, apoptosis of the cells is induced when Nef is bound to the surface of CD4+T cells of intestinal lymph node and peripheral blood and the cross-linking of the Nef molecule is caused by an anti-Nef antibody. Therefore, it is strongly suggested that binding of Nef to a Nef receptor on the CD4+T cells greatly participates in depletion of CD4+T cells in patients with HIV. Namely, pathogenesis of AIDS relates to the binding of Nef and its receptor. In addition, there is a report which suggests that Nef inhibits the production of cytokine resulting in the suppression of the immune system.

Most of the therapeutic agents for AIDS which have been used and developed so far are reverse transcriptase inhibitors such as azidothymidine, ddI, etc. and protease inhibitors, which are drugs which inhibit the growth of virus directly. In addition to these drugs, there are immunopotentiators which activate the function of the immune system depraved by AIDS and chemotherapeutic agents aimed at the treatment of symptoms such as malignant tumors and opportunistic infections caused by AIDS. Based on the above-mentioned findings on Nef, a drug which inhibits T cell apotosis caused by Nef and thereby suppresses the onset of AIDS has aroused public attention as a novel inhibitor for AIDS with a different action mechanism from those of the above-mentioned reverse transcriptase inhibitors and protease inhibitors.

Various kinds of reverse transcriptase inhibitors and protease inhibitors have been developed as a strategy to suppress AIDS. A cocktail therapy where two or more of such inhibitors are combined has been promoted in order to avoid the problems caused by the development of HIV mutation. However, there is still a strong demand for pharmaceutical agents which have a mechanism of action to suppress AIDS in addition to the direct inhibitors of viral growth. It has been recently clarified that Nef participates in invasion of the virus into cells and induces apoptosis of CD4+ T cells which play an important role in the disappearance of CD4+ cells in patients with HIV. The action is triggered by the binding of Nef to Nef-attachable protein (hereinafter, referred to as Nap) on cell walls. The actual existence of Nap has been anticipated by experiments showing the binding of Nef to CD4+ T cells or the like, however, Nap has not been specified yet.

The present invention provides a Nef-attachable protein (Nap) on the CD4+ T cell membrane which can recognize and be bound to Nef to play an important role in the onset of AIDS, a gene encoding Nap, and a monoclonal antibody against said protein.

SUMMARY OF THE INVENTION

The present inventors have prepared a specific monoclonal antibody against Nap by using a crude membrane fraction of a cell line as an antigen having high affinity to Nef. They isolated the Nap gene by utilizing said antibody and the DNA sequences of Nap was clarified. Finally, the amino acid sequences of Nap was determined successfully. Proteins having an amino acid sequence represented by SEQ ID NO:1 and functionally active homologues thereof are provided by the present invention. The proteins and DNA molecules which encode the proteins may be used in diagnosing the development of AIDS. A DNA molecule which encodes a protein having an amino acid sequence represented by SEQ ID NO:1 or which encodes a protein which is a functionally active homologue of the protein having an amino acid sequence represented by SEQ ID NO:1 may have a nucleotide sequence represented by SEQ ID NO:2 or a functionally active homologue of SEQ ID NO:2. An anti-Nef-attachable protein monoclonal antibody in accordance with the present invention has a high affinity to Molt-4 clone no. 8 cells (human CD4+ T cell line) and U937 cells (human macrophage cell line) and does not bind or attach to Raji cells (human B cell line), BT-2 cells (human gliocyte cell line) and Gin-1 cells (human fibroblast cell line). The monoclonal antibody may be a chimeric antibody having a variable region of a mouse monoclonal antibody and a constant region of a human type antibody. It may also be a human type antibody having a complementary-determining region of the mouse monoclonal antibody. The monoclonal antibodies of the present invention may be employed in pharmaceutical compositions in pharmaceutically effective amounts for the treatment of AIDS.

DETAILED DESCRIPTION OF THE INVENTION

Figure 1:
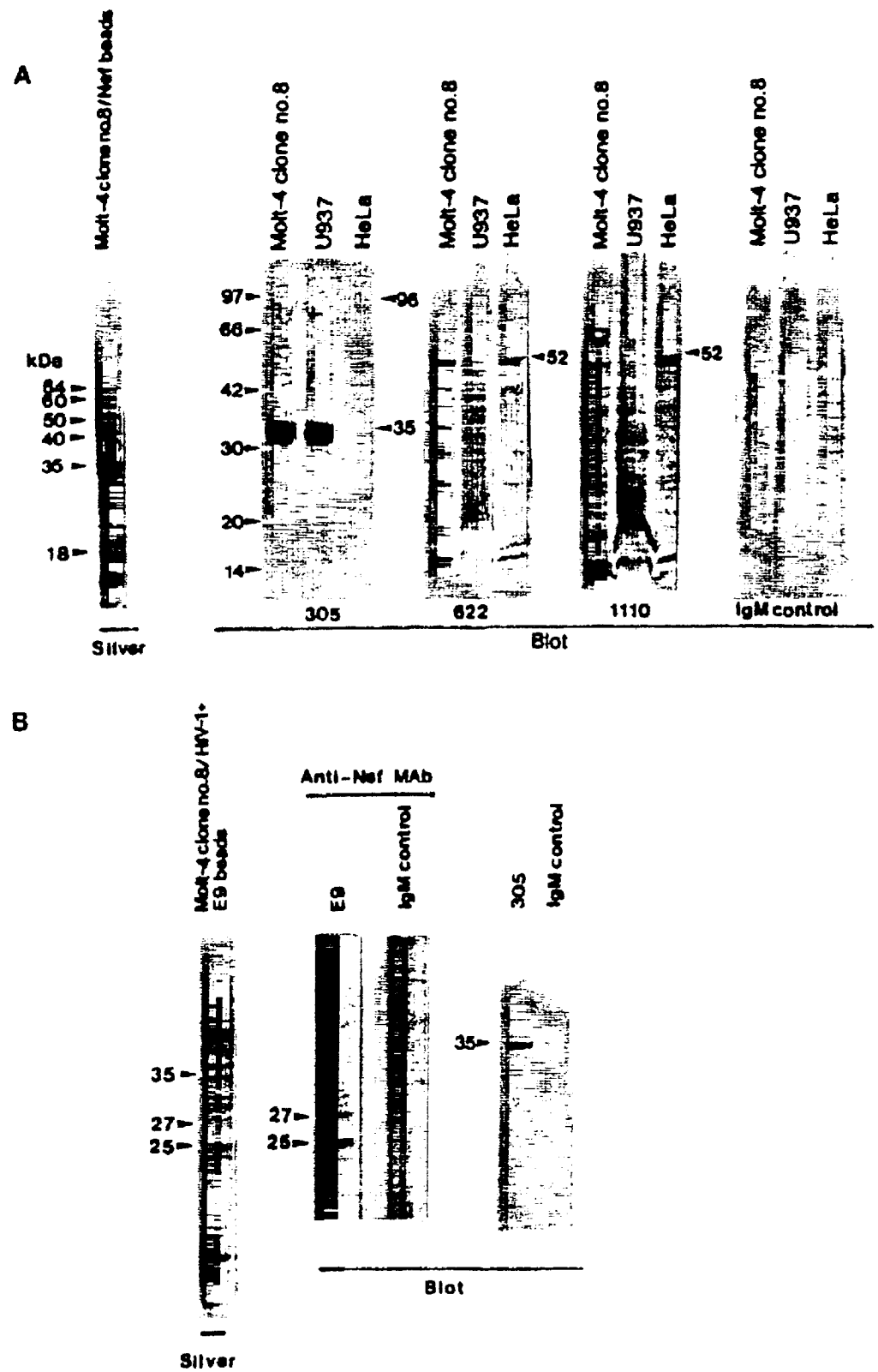
FIG. 1A shows the results of SDS-PAGE with silver staining of bound membrane fractions of Molt-4 clone no. 8 cells to Nef antigen-bearing beads, and the results of immunoblot analysis of lysates of Molt-4 clone no. 8, U937 and HeLa cells with MAbs 305, 622 and 1110.
FIG. 1B shows the results of SDS-PAGE with silver staining of bound membrane fractions of Molt-4 clone no. 8 cells infected with HIV-1 to anti-Nef E9 MAb-bearing beads, and the results of immunoblot analysis with MAbs 305 and anti-Nef MAb E9 (positive control).

The present inventors have prepared a monoclonal antibody specific to Nap by using a crude membrane fraction of a cell line which has high affinity to Nef. A cDNA clone which encodes Nap was obtained by screening a cDNA library of said cell line utilizing the specific antibody. They have elucidated the nucleotides sequence of this cDNA clone and determined the full amino acid sequence of human Nap, thus accomplishing the present invention.

As for an antigen for the preparation of a monoclonal antibody against Nap, the chance of obtaining an anti-Nap specific monoclonal antibody is increased by using the cell which has a high affinity to Nef as an antigen. Thus, high affinity to Nef means that a large number of Naps are expressed on the cell surface. Such cell line is preferred as an antigen for the preparation of the anti-Nap monoclonal antibody of the present invention because the cells contain a large amount of Nap as antigen. For example, Molt-4 clone no.8 cells (human $CD4^+$ cell line) and U937 cells (human macrophage cell line) have been reported to have high affinity to Nef. Although those cell lines are most preferable, other cell lines expressing Nap are applicable as well.

A membrane fraction of the above cells may be used as an antigen to make an affinity column where Nef is immobilized because it is preferable to use a membrane fraction which contains a larger number of Nap. In the present invention, membrane components of Molt-4 clone no.8 cells were roughly fractionated by using recombinant Nef conjugated to an insoluble carrier and used as an antigen for the preparation of anti-Nap monoclonal antibody.

The preparation of the monoclonal antibody may be carried out by using conventional methods. For example, spleen cells of an animal were obtained after the production of antibody was boosted by the sensitization of the animal with the above crude membrane fraction as antigen. Then, preparation of hybridoma and the cloning of hybridoma were carried out. To obtain a hybridoma which produces the desired monoclonal antibody of the present invention, the first selection was carried out by using an ELISA method utilizing the crude membrane fraction of Molt-4 clone no.8 cells employed as an antigen to narrow down the number of potential hybridoma. Then, flow cytometry analysis of antibodies by using Molt-4 clone no.8 cells as antigen was carried out to select a clone having high affinity to the surface of said cells. Three clones were obtained by the selection process. Finally, flow cytometry analysis using various cell lines was carried out to compare the affinity of antibodies to each cell line and a clone which produces anti-Nap monoclonal antibody of the present invention was determined. In addition, an immunoblotting method or the like using each monoclonal antibody is carried out for the confirmation of anti-Nap monoclonal antibody.

Fundamentally, purification and identification of the Nap (Nef-attachable protein) gene of the present invention can be carried out by a panning method using the anti-Nap monoclonal antibody obtained as mentioned above. Thus, in the present invention, mRNA of the Molt-4 clone no.8 cells which were used as antigen for preparation of said anti-Nap antibody is separated and a cDNA library is prepared. cDNA was integrated into plasmids and transfected to cultured cells such as Cos7 cells for the cloning of cDNA. Method for the preparation of mRNA from cells, the preparation of cDNA, integration of cDNA into plasmid, transfection into cultured cells, etc. are well known methods in the field of genetic engineering and may be carried out by setting appropriate conditions. The plasmids which were purified by repeating the above-mentioned panning method several times were transfected to Cos7 cells and the expression of Nap on the cell surface could be confirmed by flow cytometry using the anti-Nap monoclonal antibody.

Nef is strongly believed to participate in invasion of HIV virus into cells and the disappearance of $CD4^+$ T cells in patients with HIV. The action of Nef is triggered by binding of Nef to Nap on cell membranes. Thus, it has been anticipated that development of AIDS can be suppressed by inhibiting the binding of Nap to Nef. The anti-Nap monoclonal antibody of the present invention inhibits the binding of Nef to Nap and, therefore, it is a very useful agent as a new therapeutic drug against AIDS.

In the following examples, a specific description is given for a mouse antibody as an anti-Nap monoclonal antibody. However, if mouse antibody is administered to human beings as a pharmaceutical agent, the half-life of the mouse antibody in vivo is short. Moreover, there is concern about the induction of the immune system to exclude the mouse antibody, because the mouse antibody is recognized as a heteroantigen in human. In this case, human antibody against mouse antibody is produced in the human and it induces not only the neutralization of the mouse antibody but also a critical immune reaction such as an anaphylactic shock.

Accordingly, if anti-Nap monoclonal antibody of the present invention is used as a pharmaceutical agent for humans, a chimeric antibody or human-type antibody which does not negatively affect the usefulness of the mouse antibody and does not induce the above-mentioned immune reaction in humans can be used. For example, there have been many reports for methods to manufacture chimeric antibodies with mouse amino acids sequences for the region which recognizes antigen (variable region) and human amino acid sequences for the constant region except for the variable region. It is possible to manufacture chimeric antibodies which can be administered to humans from the monoclonal antibody of the present invention according to known methods such as disclosed in European Patent Publication No. 120694 B and corresponding U.S. Pat. No. 4,816,397, European Patent Publication No. 125023 B and corresponding U.S. Pat. No. 4,816,567, and International Patent Publication WO 86/01533 A, the disclosures of which are herein incorporated by reference in their entireties.

In addition, known methods for preparing human-type antibody by improving the above chimeric antibody may be employed herein. For example, a human-type antibody of the present invention may be prepared from a chimeric antibody of the present invention, by a method such as disclosed in European Patent Publication No. 239400 A, and corresponding U.S. Pat. No. 5,225,539, the disclosures of which are herein incorporated by reference in their entireties. The specific region of human type antibody which recognizes antigen directly (hypervariable region, complementary-determining region, CDR, etc.) is made of the amino acid sequences derived from mouse antibody, while the other region which is necessary for keeping the structure of the antibody is made of the amino acid sequences derived from humans. Therefore, the ratio of the non-human amino acid sequence contained in the human type antibody is lower than that of the chimeric antibody. As a result, it shows a half-life which is similar to that of human antibody in the human body. In addition, it rarely produces human anti-mouse antibody. The anti-Nap monoclonal antibody of the present invention includes said chimeric antibodies and human type antibodies as well.

The anti-Nap monoclonal antibody of the present invention including the above chimeric antibodies and human type antibodies can be characterized based upon its specificity. For example, it can be defined in terms of its specificity of antigen reactivity that: it is strongly bound to Molt-4 clone no.8 cells (human CD4+ T cell line) and U937 cells (human macrophage cell line) while it is not bound to Raji cells (human B cell line), BT-2 cells (human gliocyte cell line) and Gin-1 cells (human fibroblast cell line).

Specifically, Nap of the present invention has an amino acid sequence represented by SEQ ID NO:1 and includes proteins having an amino acid sequence wherein one or more amino acid residue(s) in the amino acid sequence represented by SEQ ID NO:1 is/are deleted, added or substituted. The term "protein having an amino acid sequence where one or more amino acid residue(s) in the amino acid sequence represented by SEQ ID NO:1 is/are deleted, added or substituted" means polypeptides (proteins) which are converted without decreasing the functions of human Nap of the present invention and includes naturally produced mutant polypeptides and artificially modified mutant polypeptides. Thus, affinity to Nef is listed as a specific function of Nap and this function can be confirmed by conducting a binding test to Nef using the converted (mutant) peptide.

Thus, embodiments of the present invention, include proteins which are biologically functional homologues of SEQ ID NO: 1, and DNA molecules having nucleotide sequences which encode a protein of SEQ ID NO: 1 or which encode a biologically functional homologue of SEQ ID NO: 1. The DNA molecules may have a nucleotide sequence represented by SEQ ID NO: 2, or may have a nucleotide sequence which is a biologically functional homologue of SEQ ID NO: 2. Biologically functional homologues, or functionally active homologues may be ascertained by those ordinarily skilled in the art without undue experimentation using tests or assays for affinity, attachment or binding to Nef as a specific function of Nap, as described, for example, herein. The deletion, addition, and substitution of amino acid residues in SEQ ID NO: 1 or of the nucleotides in SEQ ID NO: 2 may be conservative, with no significant loss, or with little or no loss of biological activity, such as conservative substitutions described in U.S. Pat. No. 5,470,753, U.S. Pat. No. 5,559,209, and U.S. Pat. No. 5,545,618 FIG. 1. The disclosures of U.S. Pat. Nos. 5,470,753, 5,559,209, and 5,545,618 are herein incorporated by reference in their entireties.

In an embodiment of the present invention, the biologically functional homologues or functionally active homologues of the proteins of SEQ ID NO:1 and the nucleotides of SEQ ID NO:2 are produced by conservative substitution of one or more amino acids or is produced by incorporation of one or more synthetic amino acids, amino acid analogs, peptidomimetic compounds or modified amino acids into the protein. For example, the amino acids can be modified or derivatized by phosphorylation, carboxymethylation, acylation, glycosylation and other methods known to the ordinary skilled artisan.

The present invention is further illustrated by the following non-limiting examples wherein all parts, percentages and ratios are by weight, all temperatures are in ° C., and all reactions are conducted at about atmospheric pressure unless indicated to the contrary:

EXAMPLE 1

Preparation of Anti-Nap Monoclonal Antibody

In this example, an anti-nap monoclonal antibody is prepared using a crude membrane fraction as an antigen. Crude membrane fractions are prepared, anti-Nap monoclonal antibodies (Mabs) are prepared from the membrane fractions, a monoclonal antibody is selected which is specific to Nap, and a Nap candidate is investigated using the monoclonal antibody:

(1-1) Preparation of Crude Membrane Fractions as Antigen

Packed cells ($1\times10^9$) of Molt-4 clone no.8 were lysed by sonication in 10 mM Tris-HCl (pH 8.0) containing 1 mM ethylenediaminetetraacetic acid (EDTA) and 50 mM phenylmethylsulfonylfluoride (PMSF). After centrifugation at 800×g for 10 minutes, the supernatant was centrifuged at 60,000×g for 30 minutes. The pellet was incubated for 30 minutes on ice in a lysis buffer consisting of 0.05% Nonidet P-40 (NP-40), 150 mM NaCl and 0.1 mM PMSF in 100 mM Tris-HCl. The lysate, after being clarified by centrifugation, was incubated for 2 hours on ice with purified N-terminal truncated Nef baculo-recombinant protein coupled to Affi-Gel 10 (Bio-Rad, Richmond) as described previously [Otake et al., J. Immunol., vol. 153, 5826–5837 (1994)]. After washing the gel three times with 0.1 M Tris-HCl (pH 7.6) containing 50 mM NaCl and 0.5% NP-40, the gel was packed in a column and elution was performed with 0.1 M Tris-HCl (pH 6.0) containing 3 M KSCN and 50 mM NaCl. Fractions containing the eluted protein were dialyzed, concentrated and analyzed by SDS-PAGE. These fractions were used for immunization of mice as the crude membrane fraction.

(1-2) Preparation of Monoclonal Antibodies

Anti-Nap monoclonal antibodies (MAbs) were prepared by immunizing BALB/C mice with said membrane fractions of Molt-4 clone no.8 cells prepared in Example 1-1. The crude membrane fractions of the cells (50 μg protein) were mixed with an equal volume of complete Freund's adjuvant, and were subcutaneously injected into the mice. One month later, the same sample was further injected subcutaneously without adjuvant four times at one week intervals. On the seventh day after the final injection, the spleens were harvested and then used for hybridization. The details of the hybridization procedure were reported previously [Fujii et al., Vaccine, vol. 11, 1240–1246 (1993)]. The production of MAbs was primarily screened by ELISA with anti-mouse immunoglobulin. The MAbs in ascites fluid were used for all experiments after purification by Sephadex G-200 chromatography.

(1-3) Selection of Monoclonal Antibody

Mouse MAbs were prepared by immunization with the membrane protein fractions from the Molt-4 clone no.8 cells as antigens and a mouse hybridoma was cloned. At first, 156 clones producing Abs were selected by ELISA from a total of 2,014 of clones. By flow cytometry using Molt-4 clone no.8 cells, three clones (MAb 305, MAb 622 and MAb 1110), which strongly reacted to Molt-4 clone no.8 cell surface, were isolated. Further, the reactivity of the three MAbs to the surface of various human cell lines and the results are shown in Table 1 below.

The values in Table 1 are the percentages of positive cells and were calculated by the results of histograms using flow cytometry. The zero points were adjusted to values of the negative controls with normal mouse IgM Abs. All experimental results are represented as the means of triplicate samples in Table 1:

TABLE 1

Reactivity of Three Mabs to the Surface of Various Human Cell Lines

| Human cell lines | Mab 305 | Mab 622 | Mab 1110 |
|---|---|---|---|
| Molt-4 clone no.8 | 61.7 | 51.8 | 36.6 |
| Molt-4 | 5.5 | 18.1 | 10.4 |
| JM | 15.5 | 49.3 | 9.2 |
| Sup-T1 | 0.0 | 65.8 | 16.1 |
| SKW-3 | 23.5 | 10.1 | 12.3 |
| CEM | 0.0 | 5.8 | 0.9 |
| MT-4 | — | 5.1 | 1.9 |
| H9 | — | 1.4 | 1.2 |

TABLE 1-continued

Reactivity of Three Mabs to the Surface of Various Human Cell Lines

| Human cell lines | Mab 305 | Mab 622 | Mab 1110 |
| --- | --- | --- | --- |
| Jurkat | 0.0 | 24.0 | 3.9 |
| K562 | 0.0 | 0.3 | 0.1 |
| U937 | 69.1 | 0.6 | 0.5 |
| BT-2 | 0.0 | 15.4 | 0.0 |
| Raji | 0.0 | 0.0 | 0.0 |
| Gin-1 | 0.0 | 35.7 | 18.4 |
| HeLa | 0.0 | 54.9 | 15.6 |

As shown in Table 1, in the three MAbs finally selected, MAb 305 strongly reacted to U937 cells, typical human macrophages which are highly infected by HIV, as well as Molt-4 clone no.8 cells. MAb 305, however, did not react to human B cells (Raji), gliocytes (BT-2) and fibroblasts (Gin-1). Therefore, it was apparently shown that MAb 305 has the same binding specificity as Nef protein, i.e., the Nef protein targets $CD4^+T$ cells and does not react to other cells including B cells. Binding assays between biotin conjugated Nef protein and Molt-4 clone no.8 or U937 cells were performed as described previously [Otake et al., 1994 (see above)] in the presence of MAb 305. Binding of Nef protein to both cells was inhibited by MAb 305 in dose-dependent manner. These results suggested that MAb 305 is an antibody specific to Nap (Nef-attachable protein).

(1-4) Investigation of Nap Candidate by Using Mabs (A) Membrane fractions from Molt-4 clone no.8 cells were precipitated with N-terminal truncated Nef protein (NL43, 34–206 amino acids) conjugated to Affi-Gel 10. The eluents were subjected to SDS-PAGE and the gel was stained with silver. The lysates of Molt-4 clone no.8, U937 and HeLa cells were analyzed by immunoblotting with MAbs 305, 622 and 1110, and normal mouse IgM antibody as a control.

As shown in FIG. 1A, bands at molecular weights of approximately 18, 35, 40, 50, 60 and 64 kDa were immunoprecipitated with Nef antigen-bearing beads from the membrane fractions of Molt-4 clone no.8 cells. Control beads did not precipitate any bands. By immunoblot analysis with MAb 305, the MAb reacted strongly with an approximately 35 kDa band and weakly with a 96 kDa band from Molt-4 clone no.8 and U937 cell lysates, but did not react to HeLa cell lysate. Both MAbs 622 and 1110 reacted to about 52 and 14 kDa bands of Molt-4 clone no.8 and HeLa cell lysates and weakly react to U937 cell lysate. Control mouse IgM Abs did not react to lysate of the three cells.

(B) Membrane fractions from Molt-4 clone no.8 cells infected with HIV-1, NL43 strain, were incubated with Affi-Gel 10 coupled to anti-Nef E9 MAb, and were precipitated. The eluents were analyzed by SDS-PAGE with silver staining and by blotting with the MAb E9 (positive control) and MAb 305. Normal mouse IgM was used as a negative control.

A result of the experiment is shown in FIG. 1B, several proteins were precipitated and the bands were visualized by SDS-PAGE with silver staining. The 35 kDa cellular protein band in the precipitants was stained by MAb 305 but not stained by normal mouse IgM (control). A positive control MAb E9 (anti-Nef MAb) stained only 25 and 27 kDa Nef protein bands. These observations suggested that MAb 305 reacted with a cellular 35 kDa protein.

EXAMPLE 2

Isolation and Identification of Nap and Gene Encoding Nap

As with the preparation of specific anti-Nap antibody as described above in Example 1, Molt-4 clone no.8 cells were used as a starting material. A cDNA library was prepared and Nap gene was selected and identified:

(2-1) Preparation of cDNA Library

Total RNA was prepared from Molt-4 clone no.8 cells by using Messenger RNA Isolation Kit (Stratagene). Poly(A) RNA was selected by oligo(dT)-cellulose column chromatography. Synthesis of cDNA primed random hexamer oligonucleotides ($pdN_6$) and oligo(dT) were performed with c-CLONE II cDNA Synthesis Kit (Clontech). After treatment of S1 nuclease following a Klenow polymerase reaction, Bst X1 nonpalindromic adaptor was ligated. Size fractionation was performed by Sephadex G-50, and then cDNA was ligated to Bst X1-digested pCDM8 vector (Invitrogen). About $5 \times 10^5$ independent clones from an oligo (dT)-primed cDNA library mixed with $5 \times 10^5$ clones from a random hexamer-primed cDNA library were obtained from transformation of MC1061/P3 cells (Invitrogen), and used for transfection of Cos7 cells.

(2-2) Isolation of cDNA Clones by Panning and Nucleotide Sequencing

The cDNA clones encoding Nap were basically isolated by a panning method. Briefly, Cos7 cells ($1 \times 10^6$) were transformed with the cDNA inserted in pCDM8 plasmid by lipofectin (Gibco) according to a conventional method and cultured for 72 hours at 37° C. in 6 cm dishes with RPMI-1640 containing 10% Nu serum IV (Becton Dickinson). The cells were detached by PBS/EDTA and resuspended in 5 ml of cold PBS/EDTA containing 10 μg/ml of anti-Nap MAb 305. After incubation on ice for 1 hour, the cells were centrifuged and resuspended in 5 ml of cold PBS/EDTA supplemented with 1% FBS, then distributed into four 6 cm panning plates precoated with 10 μg/ml of goat anti-mouse IgM (Cappel). After attaching cells to the plates for 3 hours at room temperature, non-adherent cells were removed by gently washing three times with PBS/EDTA containing 1% FBS. The extrachromosomal DNA was prepared from adhered cells according to the Hirt method.

In detail, after removing PBS/EDTA from the plates, 0.6% SDS containing 10 mM EDTA was added and the plates were incubated for 20 minutes at room temperature. The lysates were collected and NaCl was added to adjust its concentration to 1 M. The mixtures were incubated at 4° C. overnight and then centrifuged. The supernatants were extracted with phenol-chloroform. The DNA was recovered by ethanol precipitation. MC1061/P3 cells were transformed with the DNA and about $1 \times 10^5$ colonies were obtained. The total plasmid DNAs were extracted from the colonies obtained by the first panning. The plasmid DNAs were purified and used for the next transformation and panning methods. This procedure was repeated three times, and plasmid DNAs were prepared from four individual clones after the final panning. The obtained clones in pCDM8 plasmids were cut with Xho I and the fragments were recloned into the Xho I site of pBluescript SK (+) (Stratagene) by T4 ligase (pBFO clones). These clones were sequenced by the ABI PRISM T3, T7 and -21M13 Dye Primer Cycle Sequencing Kit (Perkin Elmer) with 373 DNA Sequencing System (Applied Biosystem).

The plasmids picked after said final panning were transfected into Cos7 cells. The plasmids were selected as to whether Nap expression on the Cos7 cell surface is positive or not by flow cytometry with anti-Nap MAb 305. The transfected Cos7 cells reacted with MAb 305, but untreated Cos7 cells did not react with MAb 305 at all. By this selection, four positive clones (FO 25, 32, 57 and 75) were obtained. By the nucleotide sequencing, FO 75 contained the nucleic acid sequence represented by SEQ ID NO:2, full length open reading frame. Only one band was detected by Northern blot analysis when using FO 75. According to the results, FO 75 is identified as a clone containing a Nap gene. The detected gene has a nucleic acid sequence having a TAA termination codon in addition to the nucleic acid sequence represented by SEQ ID NO:2.

It was suggested that the protein consisting of the amino acid sequence (286 amino acids) represented by SEQ ID NO:1 was a Nap, and the calculated molecular weight of the protein portion is approximately 32.6 kDa. As mentioned above, we identified a 35 kDa protein in membrane fractions from Molt-4 clone no.8 cells which specifically reacted to MAb 305 (anti-Nap monoclonal antibody) and suggested this protein was a Nap protein candidate. The molecular mass of the amino acid sequence (SEQ ID NO:1) encoded by nucleic acid sequence represented by SEQ ID NO:2 is approximately 32.6 kDa. The molecular mass of the Nap protein candidate, 35 kDa, corresponds well to that of the glycosylated peptide of 32.6 kDa protein.

(2-3) Expression of Nap Gene Candidate

The above Nap gene in pMAMneo plasmid was transfected in HeLa cells and selected with G418 (Geneticin). Gene expression was examined by flow cytometry. The cell surface of G418 resistant Nap 3201 HeLa positively reacted with anti-Nap MAb 305 after treatment with dexamethasone. The Nef-binding assay was performed with the Nap 3201 cells. NL43 Nef protein also attached to the Nap 3201 cell surface. Cell rosettes were also formed between Nap 3201 cells and Molt-4 infected with LAV-1, which cell surface positively reacted with anti-Nef MAb E9, but no clustering of cells was observed in a mixture of Nap 3201 and uninfected Molt-4 cells. The rosette formation was inhibited by treatment of anti-Nap MAb 305.

As mentioned above, it is believed that Nef participates in invasion of virus into cells and strongly participates in the disappearance of $CD4^+$ T cells in a patient with HIV due to the induction of apoptosis of the $CD4^+$ T cells. The action of Nef is triggered by the binding of Nef to the Nef-attachable protein (Nap) on the cell membrane. Thus, it is believed that Nap, as a specific protein on the $CD4^+$ T cell membrane which can recognize Nef, plays an important role in the infection of HIV and the development of AIDS.

The present invention specifies Nap as an important factor for the infection of HIV and the development of AIDS, identifies its nucleotides sequence and offers the monoclonal antibody specific to Nap. Since the anti-Nap monoclonal antibody inhibits the binding of Nef to Nap, it can be used as a new therapeutic agent for AIDS. In addition, it can be applied for the diagnosis of AIDS by clarifying the relation between the expressed amount of Nap and the development of AIDS. Nap can be utilized for binding experiments to Nef. It is useful for the development of novel therapeutic agents for AIDS based upon a mechanism of action which inhibits the attachment of both factors. The monoclonal antibodies of the present invention may be employed in pharmaceutical compositions in pharmaceutically effective amounts for the treatment of AIDS. Also, the anti-Nap monoclonal antibody may be employed for the development of new inhibitors against the onset of AIDS by a mechanism of action different from that of reverse transcriptase inhibitors or protease inhibitors.

What is claimed is:

1. A DNA molecule which encodes a protein represented by SEQ ID NO:1 or which encodes a protein having an amino acid sequence where one amino acid residue in the amino acid sequence represented by SEQ ID NO:1 is deleted, added or substituted, wherein said protein binds to Nef.

2. A DNA molecule as claimed in claim 1 which encodes a protein having an amino acid sequence where one amino acid residue in the amino acid sequence represented by SEQ ID NO:1 is deleted, added or substituted.

3. A DNA molecule which encodes a protein having an amino acid sequence represented by SEQ ID NO:1.

4. A DNA molecule having a nucleotide sequence represented by SEQ ID NO:2.

5. A DNA molecule which encodes a protein represented by SEQ ID NO:1 or which encodes a protein having an amino acid sequence where one amino acid residue in the amino acid sequence represented by SEQ ID NO:1 is deleted, added or substituted.

6. A DNA molecule according to claim 5 wherein said molecule has a nucleotide sequence consisting essentially of a nucleotide sequence represented by SEQ ID NO:2.

* * * * *

SEQUENCE LISTING

<160> NUMBER OF SEQ ID NOS: 2

<210> SEQ ID NO 1
<211> LENGTH: 286
<212> TYPE: PRT
<213> ORGANISM: Human lymphoblast

<400> SEQUENCE: 1

```
Met Glu Lys Tyr Leu Met Tyr Ser Ala Leu Thr Arg Ala Val Thr Leu
 1               5                  10                  15

Ser Asp Glu Trp Thr Glu His Lys Ala Phe Ser Gln Lys Ser Phe Phe
                20                  25                  30

Gln Phe Leu Thr Glu Asp Ile Pro Phe Phe Thr Ile Ala Leu Tyr Trp
            35                  40                  45

Leu Pro Asn Ile Thr Leu Gln Ile Pro Gln Ser Ile Leu Ser Glu Ser
        50                  55                  60

Phe Arg Glu Thr Ala Leu Cys Ser Leu Asn Ser Ser His Gly Ile Val
 65                  70                  75                  80

Ala Phe Pro Ser Arg Ser Arg Ser Leu Arg Leu Phe Leu Trp Asn Ser
                85                  90                  95

Gln Ile Asp Ile Trp Lys Pro Ile Glu Val Tyr Gly Ala Lys Gly Asn
            100                 105                 110

Ile Leu Arg Glu Lys Leu Lys Arg Ile Phe Leu Gly Asn Cys Phe Val
        115                 120                 125

Phe Cys Gly Phe Ile Ser Gln Ser Tyr Ser Phe Leu Leu Lys Lys Pro
    130                 135                 140
```

```
Phe Ala Lys Ala Val Ser Cys Gly Ile Cys Lys Val Val Phe Gly Ser
145                 150                 155                 160

Pro Ser Arg Ala Arg Val Lys Lys Glu Ile Ser Ser Val Lys Thr Trp
                165                 170                 175

Lys Glu Ala Ser Glu Asn Leu Leu Cys Val Leu Leu Ile His Leu Thr
            180                 185                 190

Glu Leu Gln Leu Ser Pro Gln Glu Ala Val Tyr Tyr Gly Cys Ser Cys
        195                 200                 205

Gly Ile Cys Lys Val Ile Phe Gly Ser Pro Glu Arg Ala Met Val Lys
            210                 215                 220

Lys Glu Thr Ser Tyr Asp Lys Asn Trp Lys Glu Ala Phe Cys Glu Thr
225                 230                 235                 240

Ala Leu Cys Ser Val Asn Ser Ser His Arg Ile Thr Ala Phe Pro Ser
                245                 250                 255

Arg Ser Leu Cys Leu Arg Leu Leu Leu Trp Asn Phe Gln Ser Asp Ile
            260                 265                 270

Leu Lys Pro Leu Glu Ser Tyr Gly Glu Lys Gly Asn Ile Leu
        275                 280                 285

<210> SEQ ID NO 2
<211> LENGTH: 858
<212> TYPE: DNA
<213> ORGANISM: Human lymphoblast
<220> FEATURE:
<223> OTHER INFORMATION: cDNA library of Human Leukemia Lymphoblast

<400> SEQUENCE: 2
atggaaaaat atttgatgta tagtgccttg actagagctg taactctgtc agatgaatgg      60
acagaacaca aagcattttc tcagaaatct tttttccagt ttttaactga agatattccc     120
tttttcacca tagccctcta ttggcttcca aatatcacct acaaattcc acaaagcatt     180 cttagcgaaa gcttccgaga aacggcattg tgttctctta attcatctca cggaattgta     240 gctttccect caagaagccg atcactaaga ctgttcttgt ggaattcgca aattgatatt     300
tggaagccca tagaggtcta tggtgcaaaa ggaaatatcc taagagaaaa actgaaaaga     360
atctttctgg gaaactgctt tgtgttctgt ggattcattt cacagagtta cagctttctc     420
ctcaagaagc cttttgcaaa ggctgttcct tgtggcattt gcaaagtggt atttggaagc     480
ccatcaaggg ctagggtgaa aaaggaaata tcttccgtta aaacctggaa agaagcttct     540
gagaacctgc tttgtgttct gttaattcat ctcacagagt tacagctttc ccctcaagaa     600
gccgtttatt acggctgttc ttgtggaatt tgcaaggtga tatttggaag cccagagagg     660
gctatggtga aaaaggaaac atcctatgat aaaaactgga agaagctttt ctgcgaaact     720
gctttgtgtt ctgttaattc atctcacaga attacagctt tcccttcaag aagcctctgc     780
ctaagactgt tgttgtggaa ttttcaaagt gatattttaa agcccttaga gagctatggt     840 gaaaaggaa atatccta                                                    858
```